United States Patent
Naegele

(12) 
(10) Patent No.: US 6,428,962 B1
(45) Date of Patent: Aug. 6, 2002

(54) NUCLEIC ACID COLLECTION BARRIER METHOD AND APPARATUS

(75) Inventor: Bernard G. Naegele, Cincinnati, OH (US)

(73) Assignee: DNA Analysis, Inc., Cincinnati, OH (US)

( * ) Notice: Subject to any disclaimer, the term of this patent is extended or adjusted under 35 U.S.C. 154(b) by 0 days.

(21) Appl. No.: 09/781,873

(22) Filed: Feb. 12, 2001

(51) Int. Cl.[7] ............................ C12Q 1/68; C12P 19/34
(52) U.S. Cl. ............................................ 435/6; 435/91.2
(58) Field of Search ...................... 435/6, 91.2; 206/44, 206/219

(56) References Cited

U.S. PATENT DOCUMENTS

| | | | | |
|---|---|---|---|---|
| 4,279,863 | A | 7/1981 | Friehler | 422/102 |
| 4,690,801 | A | 9/1987 | Anderson | 422/68 |
| 4,865,813 | A | 9/1989 | Leon | 422/101 |
| 4,889,692 | A | 12/1989 | Holtzman | 422/102 |
| 5,103,836 | A | 4/1992 | Goldstein et al. | 128/760 |
| 5,119,830 | A | 6/1992 | Davis | 128/771 |
| 5,152,965 | A | 10/1992 | Fisk et al. | 422/102 |
| 5,238,649 | A | 8/1993 | Nason | 422/58 |
| 5,266,266 | A | 11/1993 | Nason | 422/58 |
| 5,283,038 | A | 2/1994 | Seymour | 422/101 |
| 5,362,654 | A | 11/1994 | Pouletty | 436/518 |
| 5,403,551 | A | 4/1995 | Galloway et al. | 422/58 |
| 5,411,876 | A | 5/1995 | Bloch et al. | 435/91.2 |
| 5,413,924 | A | 5/1995 | Kosak et al. | 435/177 |
| 5,424,040 | A | 6/1995 | Bjornsson | 422/101 |
| 5,425,921 | A | 6/1995 | Coakley et al. | 422/102 |
| 5,449,494 | A | 9/1995 | Seeney | 422/100 |
| 5,477,863 | A | * 12/1995 | Grant | 128/749 |
| 5,496,562 | A | 3/1996 | Burgoyne | 424/488 |
| 5,500,339 | A | 3/1996 | Fuller et al. | 435/6 |
| 5,565,339 | A | * 10/1996 | Bloch et al. | 435/91.2 |
| 5,576,197 | A | 11/1996 | Arnold | 435/91.2 |
| 5,618,664 | A | 4/1997 | Kiessling | 435/2 |
| 5,629,154 | A | 5/1997 | Kim et al. | 435/6 |
| 5,643,764 | A | 7/1997 | Kosak et al. | 435/91.1 |
| 5,667,985 | A | 9/1997 | O'Leary et al. | 435/29 |
| 5,714,390 | A | 2/1998 | Hallowitz et al. | 436/526 |
| 5,753,186 | A | 5/1998 | Hanley et al. | 422/101 |

OTHER PUBLICATIONS

Ausubel FM et al. Short Protocols in molecular biology. 4th edition, pp. 15–23 to 15–26 and A–25, 1999.*

* cited by examiner

*Primary Examiner*—Jeffrey Fredman
*Assistant Examiner*—Suryaprabha Chunduru
(74) *Attorney, Agent, or Firm*—Wood, Herron & Evans, L.L.P.

(57) ABSTRACT

An apparatus and method for temporally regulating analysis of nucleic acids in a specimen. The specimen, such as blood or hair, is contained in a vessel pre-packaged with all reagents needed for the analysis, having one or more barriers that can be selectively breached. Preferably, the barrier is a wax having a discrete melting point. The vessel may be stored until specimen is added, then the vessel containing the specimen can again be stored. Breaching the barrier allows the user to select when reagents will contact the specimen. A number of barriers can be incorporated to segregate a number of reagents. This invention provides a simple, self-contained and portable vessel for collecting, transporting, and processing a specimen for nucleic acid analysis at a desired time. The invention also avoids sample and environmental contamination.

7 Claims, 3 Drawing Sheets

NUCLEIC ACID COLLECTION BARRIER METHOD AND APPARATUS

FIELD OF THE INVENTION

This invention relates to a method and apparatus to temporally regulate analysis of a nucleic acid.

BACKGROUND OF THE INVENTION

For nucleic acid analysis of biological samples, the collected samples are routinely stored in various containers. After collection of the specimen, such as blood or hair, the container is usually sealed to isolate the specimen from the environment until analysis is performed. If analysis is postponed or if off-site analysis is to be performed, some samples may be maintained in a controlled environment in order to sustain specimen integrity. Further, the container must be rugged enough to withstand transit and storage without compromising the specimen. For example, samples collected at crime scenes must be accurately identified and described, and transported to a lab for subsequent analysis.

The potential for error in maintaining, labeling, handling, etc. a sample increases with the number of manipulative steps involved. Sample contamination is a concern since, as the specimen is processed, the sample is manipulated with the risk of identification error and/or sample contamination from exogenous nucleic acid, as nucleic acids are ubiquitous and contamination may occur from innocuous sources such as dust. Likewise, environmental contamination may be a concern, since a blood sample could contaminate the surrounding environment. Each time that the specimen is transferred, manipulated, etc., there is an opportunity to misidentify the specimen, contaminate the specimen or contaminate the environment. In addition, the container or specimen could be potentially misidentified or misplaced with each handling step, resulting in incorrect or incomplete sample identification.

Biological samples often are subjected to nucleic acid analysis to identify the source of the sample, or to identify one or more features of a sample. A standard analytical tool for nucleic acid analysis of specimens is the polymerase chain reaction (PCR). The basis of PCR is that it exponentially multiplies the quantity of nucleic acid extracted from a specimen to generate a quantity sufficient for analysis. PCR requires multiple reagents appropriate for amplification, such as a buffer, all four deoxyribonucleoside triphosphates (dNTP) (i.e., adenine triphosphate or dATP, thymine triphosphate or dTTP, cytosine triphosphate or dCTP, and guanine triphosphate or dGTP), magnesium, a polynucleotide polymerase enzyme, and at least one oligonucleotide primer.

Initially, nucleic acid is extracted from a specimen and added to the above reagents. The nucleic acid is denatured at a temperature between 90° C. and 100° C. to create two single-stranded polynucleotides that serve as templates. Primers then anneal to each nucleic strand at a temperature between 40° C. and 75° C. to demarcate a target sequence for the polymerase-catalyzed attachment of the appropriate dNTP. Repeated cycling of these processes (thermal cycling) results in quantities of nucleic acid sufficient for analysis.

Since PCR exponentially multiplies any nucleic acid present, whether endogenous or exogenous to the sample, samples to undergo PCR must be handled with the utmost care. Any exogenous nucleic acid present not only contaminates the specimen, but will be amplified during PCR, yielding an incorrect analysis. Since any contaminant nucleic acid is amplified, it is easy to appreciate why even trace contamination of the sample is fatal to obtaining an accurate result.

A unitary container is important for increasing the specificity of the PCR amplification and for increasing the shelf life of any pre-mixed PCR reagents in the container. U.S. Pat. No. 5,411,876 discloses a technique preparatory to PCR that interposes a barrier into the PCR reaction vessel. The barrier in the '876 patent is composed of a hydrophobic substance, such as a grease or wax. One purpose of the barrier is to preserve reagent concentration during heating by attempting to prevent solvent evaporating from the PCR reaction tube. The melting point of the wax is chosen so that the less-dense molten wax floats on the surface of the solvent during PCR thermal cycling. After amplification, the solidified wax seals the reagents from the environment. If the PCR reaction tube is opened after amplification, the solidified wax barrier prevents both endogenous nucleic acid from escaping and endogenous nucleic acid from comingling with the endogenous nucleic acid. A disadvantage of this method, however, is that the addition of the hydrophobic material adds a handling step that poses a risk of contamination.

A second purpose of the technique disclosed in the '876 patent is to pre-fill a PCR reaction vessel with reagents necessary for DNA amplification in a batch process. Batch processing removes a handling step by eliminating the necessity of adding the hydrophobic material during PCR thermal cycling, enables more accurate control over the addition of reagents, and creates a stockpile of PCR reaction tubes for future use. A wax barrier segregates one or more necessary reagents from the remaining reagents. The melting point of the wax is chosen such that the wax is solid at storage temperatures of about 0° C. to 5° C. Heating the PCR reaction tube above about 40° C. causes the wax to melt, releasing the sequestered reagent and initiating the PCR process. Segregation of selected PCR reagents inhibits primer oligomerization and extends the stability of the reagent mixture from only a few days to a week or more. The segregation also minimizes annealing of primers to non-target sequences, which reduces the yield of amplified target sequences. If reagents are combined prior to the start of thermal cycling, mispriming occurs in an admixture of the nucleic acid to be amplified.

A limitation of the invention disclosed in the '876 patent is that the disclosed vessel is not intended for prolonged storage of the contained reagents near room temperature. In addition, the container and method cannot be used with the intact biological specimen to be analyzed, but is limited to use with the nucleic acids that have already been extracted from the biological specimen, requiring at least one manipulation step, during which contamination or error can occur. Still another limitation is that the PCR reaction tube must be sized to fit the PCR instrument(s).

It is known to pre-fill sample containers with a reagent to conveniently process a specimen added to the container. To control exposure of the specimen added to the container, the reagent can be enclosed within a secondary frangible container contained within the primary sample container. The reagent is then released by rupture of the frangible container, and is subsequently mixed with the sample while confined within the primary sample container. One disadvantage of this method is that fragments from the frangible container can contact and hence contaminate the sample. Another disadvantage of this method is the addition of a costly manufacturing step to produce the intricate "container within a container" assembly. Although some pre-filled sample containers eliminate the frangible barrier, these are usually not amenable for use in an analytical instrument.

Thus, what is ideally desired is a simple, portable and inexpensive method and apparatus to allow the user to temporally regulate the analysis of a specimen containing a nucleic acid.

SUMMARY OF THE INVENTION

The inventive method and apparatus permit the collection, transport and identification of a specimen that contains nucleic acid, while also controlling exposure of the specimen to all reagents that will be needed for processing and analyses of the specimen using the polymerase chain reaction. By employing one or more breachable barriers to segregate one or more reagents from the specimen, the present invention permits temporal selectivity for processing and analyses. The present invention reduces fabrication costs by eliminating the need for a frangible barrier or a complicated container geometry. Many containers incorporating the present invention can be prepared by batch processing. This enables reproducible reagent compositions and reduces the cost and time involved to prepare individual containers.

Other advantages and features of the present invention will be appreciated with reference to the following drawings, detailed description, and examples.

DETAILED DESCRIPTION

Figure 1:
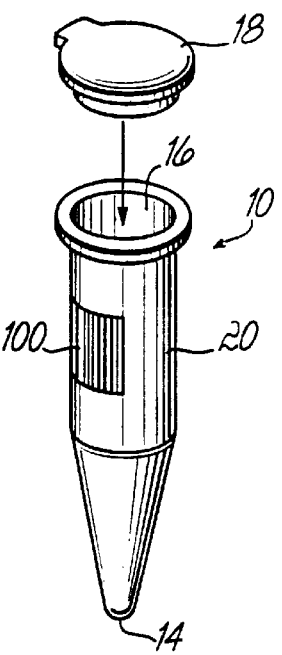
FIG. 1 is a perspective view of one embodiment of the container according to the principles of the present invention.

Referring to FIG. 1, an apparatus in accordance with the principles of the present invention includes a container 10. In one embodiment, the container 10 has a closed curved end 14, an open end 16 that can be securely sealed, such as by a tight-fitting cap 18, and a container wall 20. The open end 16 is distal to the closed end 14 so that the container wall 20 defines an enclosed volume 12. The container wall 20 must be constructed of a chemically inert material that can withstand temperatures in the range of about 20° to 100° C. Polypropylene is one such material, but other materials can also be used without departing from the spirit and scope of the present invention.

Figure 2:
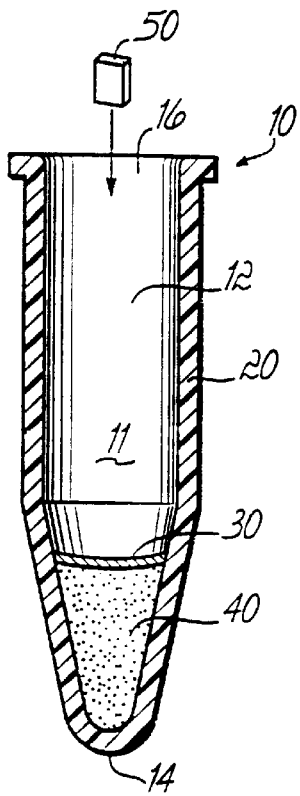
FIG. 2 is an axial cross-sectional view of the container shown in FIG. 1.

Referring to FIG. 2, container 10 incorporates a barrier 30 to isolate at least one reagent 40 from a headspace 11 above the barrier 30. One or more reagents 40 used in the polymerase chain reaction (PCR) are contained in the enclosed volume 12. The volume of reagents can vary as long as the total volume can be contained while still leaving adequate space for addition of sample, but preferably a reagent volume of about 0.5 ml is used.

The reagents can be lysing reagents, amplifying reagents, photosterilizing reagents, detecting reagents, and combinations thereof. Lysing reagents disrupt the cellular walls of a specimen containing nucleic acids. A typical combination of lysing reagents includes a buffer, a detergent, and a protease. Photo-sterilizing reagents prevent the use of nucleic acid as a template for subsequent reactions. A typical photo-sterilizing reagent includes a photo-reagent and a chelator to remove magnesium ions. Amplifying reagents, typically a buffer, four deoxyribonucleoside triphosphates, a magnesium compound, a polynucleotide polymerase enzyme and at least one oligonucleotide primer, are used to increase the amount of nucleic acid in a specimen by replicating the nucleic acid. Detecting reagents are substances that carry an analytical signal generator, for example, a radioisotope or magnetic particles, that facilitates detection and separation of the amplified nucleic acid from other components of the reaction mixture.

After reagents 40, such as those previously mentioned, are added to the container 10, barrier 30 is interposed between the reagents 40 and the headspace 11. The barrier is such that if a specimen 50 is introduced into the headspace 11 above the barrier 30, the reagents 40 do not contact the specimen and thus cannot react with it. The barrier 30 is composed of a hydrophobic material that, when breached, releases the reagents 40 from confinement. Breach of the barrier can occur by any number of methods to change the physical integrity of the barrier 30, but most preferably occurs by application of an energy source such as heat. The container 10 is then agitated by either a manual or automated method, to mix the specimen with the reagents 40 and to promote a complete reaction.

In one embodiment, the barrier 30 is generated by adding molten wax to the container 10 containing the desired reagents 40. A volume of wax of about 0.050 ml is adequate for a container that can accommodate a volume of 0.5 ml of reagent. The wax is then allowed to solidify and a specimen 50 is added to the container 10. The container 10 is then closed in a manner to eliminate release of the specimen 50 from the container 10 and to prevent contamination of the specimen 50 by extraneous agents or objects. At a desired time, the barrier 30 is breached by heating the container 10 above the melting point of the wax barrier 30. Since the wax is less dense than the solution, the molten wax will float on the surface of the solution. As the container 10 cools, the wax will solidify to form a seal that overlaps and hence protects the mixture of sample and reagents.

Figure 3:
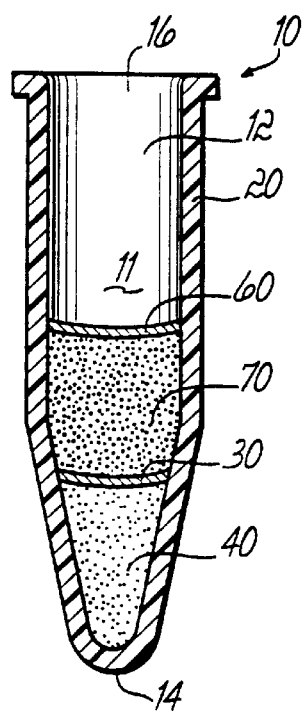
FIG. 3 is an axial cross-sectional view of an alternate embodiment of the container according to the invention.

Referring to FIG. 3, in an alternate embodiment of the invention, a second wax barrier 60 and a second reagent 70 may be added to the container 10. In this case, a container is prepared containing reagents and barrier, as previously described. However, before addition of sample, a second reagent 70 is added to the container 10 and accumulates above the first barrier 30 in a section of the headspace 11 within the enclosed volume 12. The sample is then added.

In this embodiment, each barrier 30, 60 can be individually breached by the application of an energy source. For example, in one embodiment a second wax barrier 60 is generated by pouring molten wax having a melting point that is at least about 5° C., and preferably about 10° C. different from the melting point of the first barrier 30 into the container 10. The wax is then allowed to solidify. The melting point of the wax of the first barrier 30 must be less than the melting point of the wax of the second barrier 60 if premixing of the two reagents 40, 70 is desired before sample 50 contained within the vessel is mixed. Likewise, if the melting point of the wax constituting the first barrier 30 is greater than the melting point of the wax of the second barrier 60, the second reagent 70 will contact the sample as the container is heated and the first reagent 40 will remain confined.

It will be understood that the present invention may incorporate a plurality of wax barriers 60, each isolating a reagent 70. The melting point of each wax is discrete and chosen such that each reagent can be individually released with discretion by selecting the appropriate temperature to which the vessel is exposed.

A kit, prepared in accordance with the present invention, can be used to collect a set of specimens 50 for nucleic acid identification. The kit contains at least one of the inventive vessels, and preferably at least two vessels, as described. Specimens 50 are added to the container above the barrier 30. In one embodiment, the preferred barrier 30 is wax with a melting point of about 55° C. that has been presterilized and is in a volume of about 50 μl. The reagent is a lysing reagent that includes a buffer, a detergent, and a protease.

Typical specimens 50 inserted into the container are hair, blood or cells from the mucous membranes of the oral cavity, commonly termed buccal swabs. For hair, it is preferable to have at least about 10 to 30 hairs and the hairs must include roots. For blood, a volume of about 10–100 μl is sufficient. For mucosal cells, the cell may be obtained by swabbing the inner cheek membrane with a cotton-tipped swab and, in that case, the swab tip containing the cells may be removed from the handle of the swab and placed into the vessel 10.

A label 100 having a unique identifier, for example a bar code, and a tamper resistant seal are also affixed to each vessel 10 (FIG. 1). The vessels 10 are placed in a transport holder to which an identifier, for example 10 a bar code, and a tamper resistant seal are affixed. The containers 10 are packaged and transported to an analytical laboratory, preferably using a pre-addressed envelope. Upon receipt at the analytical laboratory, the integrity and identifier of the transport holder are verified and the receipt of the container 10 carrying the specimens 50 is noted.

For initiation of the nucleic acid analysis, the sealed tubes are transported to a clean room environment within the laboratory. After confirmation of the container identity and any other preparative steps, such as assembly of equipment, the container 10, still sealed, is heated to a temperature in the range of the melting temperature of the wax barrier 30 for a defined time. Preferably, intermittent mixing is performed during the melting process. The melted wax, being inert, does not affect either the specimen or the reagents.

Once the barrier 30 has melted to an extent whereby the specimen 50 to be analyzed and the lysing reagent make contact, the container 10 may be opened to add nucleic acid extraction reagents.

One advantage of the present invention is that it permits temporal selectivity for processing and analyses of a specimen 50. It is preferred to delay the exposure of specimen 50 to reagents until immediately before analysis. The container 10 of the present invention permits discretion over the time of mixing the specimen 50 and segregated reagents, as temperatures sufficient to breach the barrier will not occur absent application of heat.

Another advantage of the present invention is that it eliminates the need for a complex container geometry or mechanism to isolate the reagent from the specimen 50. The barrier accomplishes the same function as "container within a container" vessels, yet does not fragment upon breach as does a frangible container, and is functionally simple and relatively inexpensive in comparison. In addition, if the barrier is wax, the same wax that is used as an original barrier is used to reseal the contents in the container after processing to prevent contamination by exogenous nucleic acid.

The present invention is both cost and time saving, since fewer laboratory manipulation steps are required in specimen collection, processing, and analysis.

Specimens 50 can be collected from deceased or living humans, and specimen volume is not critical. Specimens 50 can be collected on diverse media, for example, filter paper, cotton swabs, cigarette butts, gum, or other media. The physical state of the specimen 50 is not critical, for example, coagulated blood is acceptable, thus broadening the range of specimens that can be collected. Solids or liquids may be collected and placed into the container 10. Further details and embodiments of the invention will be described in the following examples.

EXAMPLE 1

Stability of nucleic acids contained in samples contained in the inventive vessel over a one week period of time at 25° C. was evaluated. Using a vessel according to an embodiment of the invention having two wax barriers isolating separate reagents, either samples of whole blood (100 ml) or samples of hair with roots (10–20) were placed in the vessel on top of the upper wax barrier. The reagent retained by the upper wax barrier was a proteinase K solution (0.51 ml) composed of 0.4 ml TNE (1 mm Tris, pH 7.5, 50 mM NaCl, 0.5 mM EDTA), 0.025 ml sodium dodecyl sulfate (SDS) 20%, 0.075 ml sterile deionized water, and 0.010 ml proteinase K (20 mg/ml). All samples were collected and inserted into the vessels at the same time. Nucleic acid for blood and hair samples was extracted immediately and also after one week of storage at room temperature (25° C.). The stored samples simulated conditions during which specimens may be held prior to analysis, e.g., during shipment.

Extraction of nucleic acid from the samples was initiated by incubating the vessels containing the samples at 55° C. for two hours, with intermittent mixing of the samples and reagents by placing the vessels on a vortex for a few seconds every 30 minutes. The vessels were evaluated at the end of the incubation to ensure that the upper wax barrier had melted and that the specimens had mixed with the proteinase K digestion solution. Nucleic acid extraction then proceeded according to the following methods.

The vessels containing the now digested samples were incubated at 70° C. to melt the lower wax barrier and permit the formerly confined extraction reagent (phenol:chloroform:isoamylalcohol 25:24:1) (0.5 ml) to mix with the digested samples. The contents of each vessel were then mixed by briefly vortexing. The upper aqueous phase was transferred to a fresh sterile 1.5 ml test tube using a sterile pipette. Residual chloroform was evaporated by incubating the open container containing the extracted nucleic acid at about 60° C. for about 1 hour.

The extracted nucleic acid was then microconcentrated. The solution (about 500 ml) was transferred, using a sterile pipette or other means, into a Microcon 100 microconcentrator (Millipore) and centrifuged at about 500×g (about 2475 rpm) for about 15 min. A buffer solution of 10 mM Tris and 1 mM EDTA (0.2 ml) was added to the microconcentrator and centrifugation was repeated for 5 minutes using the same conditions as previously described. The microconcentrator was then inverted in a sterile 1.5 ml tube and the microconcentrate was collected by centrifugation at a maximum speed for about 2 min.

Nucleic acid in the samples was quantitated by spotting the microconcentrate on a Biodyne B membrane. Known human DNA standards of 2 ng, 1 ng, and 0.5 ng in a volume of 5 µl were placed on the membrane in order to compare the samples. About 5 µl of each sample were added to 0.15 ml of spotting solution (0.4 N NaOH, 25 mM EDTA, 0.00008% bromothymol blue). The samples were spotted onto the pre-wetted (0.4 N NaOH, 25 mM EDTA) Biodyne B membrane secured in a vacuum manifold. A vacuum was applied to the apparatus containing the membrane with the samples spotted thereon for about 1 min. to ensure that all the nucleic acid solution had been incorporated through the membrane. The membrane was placed in 50 ml of hybridization solution (5X SSPE, 0.5% w/v SDS), including 2.5 ml of 30% hydrogen peroxide ($H_2O_2$). The membrane was incubated for about 15 min. at about 55° C. with gentle agitation. The solution was removed, preferably by pouring the solution off the membrane, and 30 ml of hybridization solution containing 0.02 ml D17Z1 human specific probe was added. The membrane was incubated for about 20 min. at about 50° C. with gentle agitation. The hybridization solution was then removed as previously described, and rinsed with 100 ml wash solution (1.5X SSPE, 0.5% SDS) for 1 min. After about 1 min, 30 ml of wash solution containing 180 µl enzyme conjugate:HRP-SA was added and incubated at about 50° C. for about 10 min. with agitation. The enzyme solution was removed and the membrane washed with 100 ml of wash solution for 15 min. at about 22° C. (room temperature) with agitation. The membrane was then washed with 0.1 M sodium citrate, pH 5 for 1 min. and removed. Development solution (30 ml citrate buffer containing 1.5 ml of the chromagen:TMB and 3% $H_2O_2$ was added, and the membrane was incubated in the dark at room temperature for 20 min. The development solution was removed, and the color reaction was stopped by adding deionized water. The membrane was then photographed.

Figure 4A:
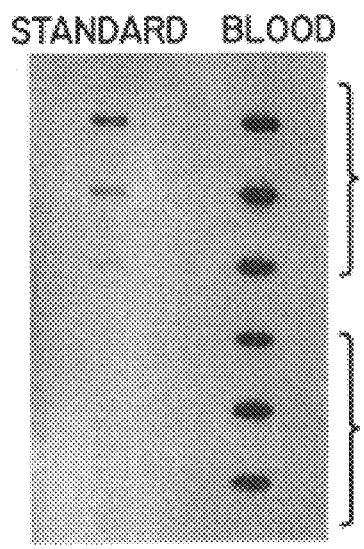
FIG. 4A is a photograph of a membrane containing nucleic acid from blood samples stored for various times according to the invention.
Figure 4B:
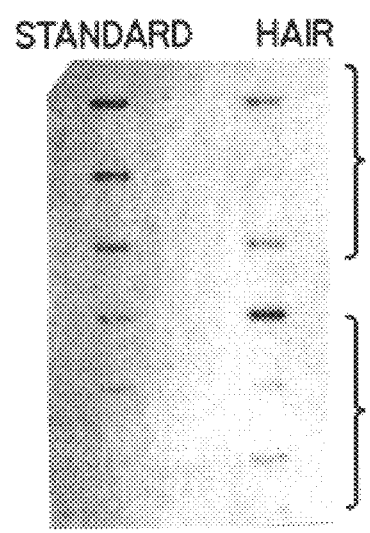
FIG. 4B is a photograph of a membrane containing nucleic acid from hair samples stored for various times according to the invention.

The results are presented in FIGS. 4A (blood) and 4B (hair). As shown in FIG. 4A, there did not appear to be any significant difference between amounts of nucleic acid that were extracted from a fresh sample of blood, as shown adjacent the upper bracket, or a sample of blood that had been stored at 22° C. (room temperature) for 1 week in the container of the present invention, as shown adjacent the lower bracket. As shown in FIG. 4B, there did not appear to be any significant difference in two of the samples between amounts of nucleic acid that were extracted from three fresh hairs, as shown adjacent the upper bracket, or a sample of three hairs that had been stored at 22° C. (room temperature) for 1 week in the vessel of the present invention, as shown adjacent the lower bracket. In one of the samples, the stored samples showed an even darker band than the freshly extracted samples.

EXAMPLE 2

Stability of nucleic acid to various temperatures was evaluated using samples of whole blood (about 100 µl), hairs including hair roots (10–20), and epithelial cells from the oral mucosa (cotton tip from a buccal swab). The blood and hair samples were placed into the vessel of the invention directly on the wax barrier segregating the extraction solution, as previously described. The cotton tip of the collection apparatus was removed from the holder and the tips were likewise placed in the vessel on the wax barrier. Vessels containing respective samples were incubated at about 4° C., 25° C., or 37° C. for 3 days. The temperatures were selected to represent standard storage or transit temperatures; simulating refrigeration conditions (about 4° C.), room temperature conditions (about 25° C.), and in vivo conditions (about 37° C.). Nucleic acids were extracted as previously described. Analysis of each sample was performed in duplicate.

Figure 5:
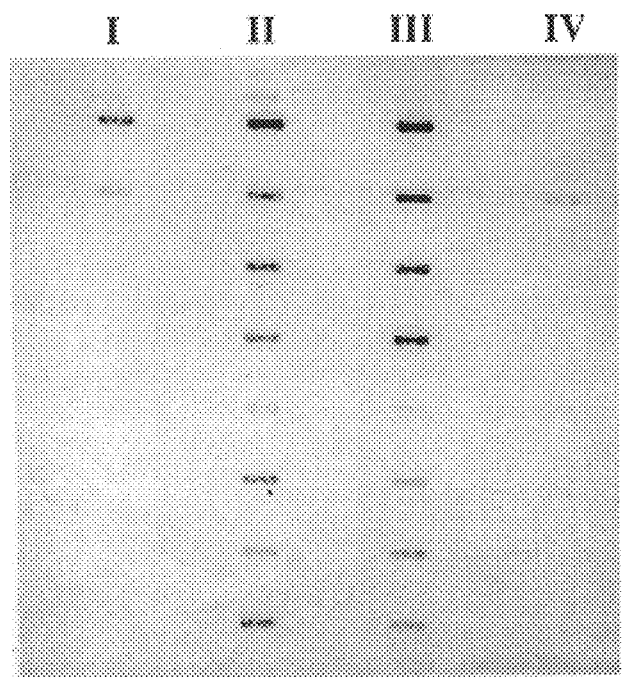
FIG. 5 is a photograph of a membrane containing nucleic acid from samples stored at various temperatures.

The results are presented in FIG. 5. In column I, from top to bottom are human nucleic acid standards of 2 ng, 1 ng, 0.5 ng, 0.25 ng, and 0.125 ng in a volume of 5 µl. In column II, from top to bottom are nucleic acid extracted from blood stored at 4° C., 25° C., and 37° C., the middle three lines sequentially represent the nucleic acid extracted by a conventional method from epithelial cells stored at 4° C., 25° C., and 37° C., and the bottom three lines sequentially represent the nucleic acid extracted by a conventional method from hair stored at 4° C. and 25° C. In column II, from top to bottom, is nucleic acid extracted from blood samples stored in the inventive vessel at 4° C., 25° C., and 37° C., the middle three lines sequentially represent the nucleic acid extracted by the barrier method from epithelial cells stored at 4° C., 25° C., and 37° C., and the bottom three lines sequentially represent the nucleic acid extracted by the barrier method from blood stored at 4° C. and 25° C. In column IV, from top to bottom are nucleic acid extracted from hair stored at 37° C. using a conventional method first (top band) and from the inventive method (second band).

As shown in FIG. 5, the results of the nucleic acid analyses indicated that samples stored either at about 4° C. or about 37° C. for three days generated similar quantities of nucleic acid, ranging from 1 to 5 ng/µl, for all three specimens. Additionally, further analyses indicated that the same quantity of DNA was generated from samples stored 3 days at 4° C., 25° C., or 37° C. (FIG. 3). For example, nucleic acid profiles from hair stored in the inventive vessel at either 4° C. or 37° C. were indistinguishable (data not shown).

Figure 6A:
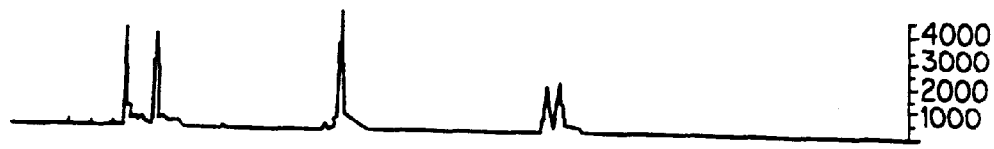
FIGS. 6A through 6F are photographs of electrophoretically separated nucleic acid profiles.
Figure 6B:
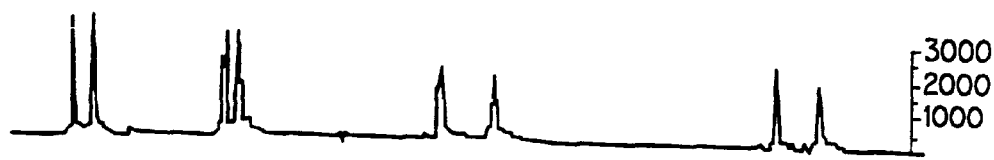
Figure 6C:
Figure 6D:
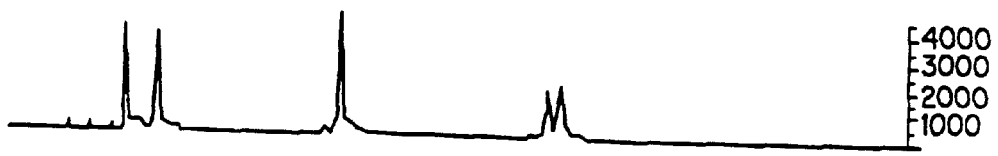
Figure 6E:
Figure 6F:

Referring to FIGS. 6A–6F, nucleic acid profiles were generated using an AmpF/STR™ Profiler Plus PCR reaction kit that amplifies ten genetic loci for purposes of human identification. FIGS. 6A–6C are the ten genetic loci for nucleic acid profiles generated from blood samples according to the inventive method. FIGS. 6D–6F are the ten genetic loci for nucleic acid profiles generated from blood samples collected by conventional organic extraction methodology, as is known to one skilled in the art. The results between the methods are virtually indistinguishable.

The container of the invention can be used for extraction and subsequent analysis of nucleic acid from either whole blood (either anticoagulated or coagulated), epithelial cells from the oral mucosa (buccal swabs), or hairs with intact roots. The nucleic acids extracted can be used to generate human profiles such as DNA profiles.

The inventive vessel allows sample and storage for subsequent nucleic acid extraction and analysis in a unitary, self-contained system. Use of the vessel reduces hands-on time, which in turn reduces the risk of contamination, benefits long term storage, is amenable to different types of samples, and is cost effective.

It should be understood that the embodiments of the present invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

What is claimed is:

1. A method for temporally regulating extraction and digestion of nucleic acid in a sample comprising providing said sample to a vessel containing reagents for said nucleic acid extraction selectively segregated from reagents for said nucleic acid digestion by a first thermally breachable barrier, said reagents also selectively segregated from said sample by a second thermally breachable barrier, and thereafter selectively breaching said first and second barriers to regulate contact of said extraction and digestion reagents with said sample.

2. The method of claim 1 wherein said digestion reagent comprises a buffer, a detergent, and a protease.

3. The method of claim 1 wherein each of said first and second thermally breachable barriers is a hydrophobic substance.

4. The method of claim 1 wherein each of said first and second thermally breachable barriers is a wax.

5. The method of claim 1 wherein said sample is selected from the group consisting of blood, hair, and epithelial cells.

6. The method of claim 1 wherein said sample contacts said digestion reagent and thereafter contacts said extraction reagent.

7. The method of claim 1 wherein said sample contacts said digestion reagent and is stored in said vessel before contact with said extraction reagent.

\* \* \* \* \*

UNITED STATES PATENT AND TRADEMARK OFFICE
CERTIFICATE OF CORRECTION

PATENT NO.    : 6,428,962 B1
DATED         : August 6, 2002
INVENTOR(S)   : Naegele It is certified that error appears in the above-identified patent and that said Letters Patent is hereby corrected as shown below:

Column 5,
Line 34, "for example 10 a bar code, and a" should be -- for example a bar code, and a --.

Column 8,
Line 14, "In column II," should be -- In column III, --.

Signed and Sealed this

Tenth Day of December, 2002

JAMES E. ROGAN
*Director of the United States Patent and Trademark Office*